United States Patent [19]

Loveless

[11] Patent Number: 4,642,410
[45] Date of Patent: Feb. 10, 1987

[54] CATALYTIC POLY ALPHA-OLEFIN PROCESS

[75] Inventor: Frederick C. Loveless, Cheshire, Conn.

[73] Assignee: Uniroyal Chemical Company, Inc., Middlebury, Conn.

[21] Appl. No.: 711,705

[22] Filed: Mar. 14, 1985

[51] Int. Cl.$^4$ ................................................ C07C 2/02
[52] U.S. Cl. ................................ 585/524; 585/522; 585/523
[58] Field of Search ........................ 585/522, 523, 524

[56] References Cited

U.S. PATENT DOCUMENTS

| | | | |
|---|---|---|---|
| 2,907,805 | 10/1959 | Bestian et al. | 585/524 |
| 3,065,220 | 11/1962 | McManimie et al. | 260/94.9 |
| 3,113,167 | 12/1963 | Sauer | 260/683.15 |
| 3,131,171 | 4/1964 | Calfee | 260/93.5 |
| 3,251,901 | 5/1966 | Bacshai | 260/683.15 |
| 3,354,139 | 11/1967 | Vandenberg | 260/94.9 |
| 3,432,513 | 3/1969 | Miller et al. | 260/93.7 |
| 3,472,910 | 10/1969 | Favis | 260/683.15 |
| 3,549,723 | 12/1970 | Favis | 260/683.15 |
| 3,634,249 | 1/1972 | Dupas et al. | 252/59 |
| 3,717,613 | 2/1973 | Ichikawa et al. | 260/63 R |
| 4,041,098 | 8/1977 | Loveless | 260/683.15 |

OTHER PUBLICATIONS

Beynon et al, Polymerization of Dec-1-ene, J. Appl. Chem. 12, Jan. 1962.

Primary Examiner—Curtis R. Davis
Attorney, Agent, or Firm—John A. Shedden

[57] ABSTRACT

Alpha-olefins are oligomerized at high yields and rapid reaction rates by using a catalyst system comprising titanium halide, an organic halide and a trialkylaluminum compound. In performing the reaction, the titanium halide and the organic halide are first admixed, preferably in monomer. The reaction is initiated by admixing the aforesaid solution with the alpha-olefin containing the alkyl aluminum component. The reaction may be performed using a variety of organic halides at a varying alkyl aluminum to titanium compound ratio.

6 Claims, No Drawings

CATALYTIC POLY ALPHA-OLEFIN PROCESS

BACKGROUND OF THE INVENTION

It is well known that alpha-olefins may be oligomerized to form poly alpha-olefins which are useful as lubricants, hydraulic fluids, and heat transfer agents. Various combinations of catalyst components have been described.

For example, Dupas et al. U.S. Pat. Nos. 3,634,249 and Sauer 3,113,167 show a combination of trialkylaluminum and titanium tetrachloride for making synthetic lubricating oils. The catalyst, prepared in a hydrocarbon solvent, is used for the copolymerization of ethylene and propylene. No organo-halide compound is present. Beynon et al., Polymerisation of Dec-1-ene, J. Appl. Chem., 12, Jan. 1962, describes the polymerization of decene using a catalyst combination of trialkylaluminum and titanium tetrachloride. Again, no organic halide is added and in both instances a very slow Ziegler catalyzed reaction occurs.

Loveless, in U.S. Pat. No. 4,041,098, oligomerizes straight chain olefins by forming a first feed containing a low molecular weight alpha-olefin and a soluble aluminum alkyl halide and a second feed containing alpha-olefin and an organic halide. He forms synthetic lubricating oils. No titanium halide component is present.

Bacskai, U.S. Pat. No. 3,251,901, illustrates the use of a three-component Ziegler catalyst system wherein a titanium compound such as titanium tetrachloride is admixed with a low molecular weight alkyl aluminum compound in an inert diluent to form the catalytic medium. Thereafter, the alpha-olefin monomer containing a small amount of allyl halide is contacted with the catalyst. The allyl halide is added in varying amounts to regulate the molecular weight of the product. The titanium tetrachloride and alkyl aluminum form a catalyst suspension which must be stirred during the reaction process. In the system described, the allyl chloride serves to reduce the viscosity of the product. Its behavior is apparently unique, since other organic halides such as carbon tetrachloride and n-propylchloride are found to have no effect.

Favis U.S. Pat. Nos. 3,472,910 and 3,549,723 make low molecular weight poly alpha-olefin polymers. The catalyst system described comprises an aluminum trialkyl, titanium tetrachloride, a tertiary alkyl halide or alkyl halo cyclopentane and ferrocene. Typically, the catalyst components are thoroughly mixed and heated to the reaction temperature in the reactor prior to the introduction of ethylene. In preparing the catalyst, the trialkyl aluminum and the chlorinated hydrocarbon are first reacted.

In Vandenberg U.S. Pat. No. 3,354,139, ethylene is polymerized to poly alpha-olefins with the addition of a halo-alkane to control the molecular weight. The catalyst components described are aluminum alkyl and titanium tetrachloride. As in the case of certain of the above references, the catalyst is formed by first admixing the aluminum alkyl and the titanium tetrachloride to obtain a suspension.

Ichikawa et al., in U.S. Pat. No. 3,717,613, while concerned with the preparation of copolymers such as acrylonitrile nitrile and butadiene of high molecular weight, shows a three-component Ziegler catalyst system comprising a trialkyl aluminum, an organic halogen compound, and a metal compound such as titanium tetrachloride. Here the catalyst is formed by first admixing the organic halogen compound with the transition metal compound, e.g. titanium tetrachloride, in a solvent and then adding the organo-aluminum compound to this admixture. Thereafter the monomers are brought into contact with the catalyst solution. The reaction, as is typical with the Ziegler type, is slow.

The use of multicomponent Ziegler catalyst systems for preparation of high molecular weight poly-olefins is shown in Miller et al. U.S. Pat. Nos. 3,432,513; Calfee 3,131,171; and McManimie 3,065,220. The Miller patent shows the production of polypropylene and teaches that the addition of an organic halide compound increases the amount of isotactic material produced. The preferred mode of addition of the catalyst components is to admix the organo-aluminum compound and the organo-halide in the inert diluent initially and thereafter to introduce the titanium halide. It is further disclosed that the first two compounds are preferably aged and in some cases heated before the titanium tetrachloride is added.

Calfee shows a catalyst system prepared by admixing a Ziegler catalyst with a solution of aluminum chloride in a lower alkyl halide. The Ziegler catalyst is formed by the reaction of a trialkyl aluminum with titanium tetrachloride. The purpose here is to obtain higher yields of solid high molecular weight polymer.

McManimie shows the use of Ziegler catalysts for making high molecular weight polyethylene. The catalyst is prepared by initially admixing the trialkyl aluminum with the titanium tetrachloride to form a catalyst suspension. To this extent, the disclosure of this patent is comparable to the Calfee patent.

BRIEF DESCRIPTION OF THE INVENTION

In accordance with the instant invention, it has been discovered that oligomers useful for synthetic lubricant applications may be prepared by reacting alpha-olefins with a three-component catonic catalyst system wherein the addition of the catalyst components to the olefins is controlled.

More specifically, the components of the instant invention comprise (1) an organic halide; (2) a transition metal halide; and (3) an alkyl aluminum compound. Particularly important is the mode of addition of the catalyst components. Firstly, the transition metal compound and the organic halide are admixed with one another generally to form a true solution, preferably in monomer. Thereafter, this solution is brought into contact with the alkyl aluminum compound which has preferably been dissolved in the monomer. This procedure should be contrasted to the prior art, where Ziegler-type catalysts are conventionally formed by the reaction of the alkyl aluminum compound with the transition metal compound. In such cases, a precipitate is invariably produced, thereby forming a catalyst with different properties than those obtained by the practice of this invention, and the reaction proceeds slowly.

The alpha-olefins which may be reacted in accordance with the teaching of the invention include those containing from 3 to 14 carbon atoms. The products of the oligomerization reaction are preferably hydrocarbon fractions boiling above 750° F. Normally, these contain oligomers containing from 35 to 350 carbon atoms. This represents a molecular weight range of from about 500 to 5000. While lower and higher boiling materials may be formed, these need not be separated.

The examples which follow clearly show the advantage of the subject invention over the prior art. For example, the Bacskai reference, while superficially similar, produces a markedly different active catalyst, one which is in the form of a precipitate resulting from the reaction of the titanium and aluminum compounds. Since this precipitate must be suspended in a solvent, it is not possible to perform a solventless oliogomerization. In contrast, this is practical by using the process of the instant invention, where the reaction between the organic halide and the titanium tetrachloride forms a true solution in monomer.

Further differences are apparent. In the practice of the invention, a variety of organo-halides may be used. Bacskai claims that only allyl chloride is useful, showing specifically that n-propyl chloride and carbon tetrachloride do not work. Note further that the allyl chloride added by Bacskai is for the express purpose of reducing viscosity, whereas the organic halide in the instant invention serves to increase the molecular weight and hence the viscosity. Most strikingly, the subject process results in extremely high conversions (uniformly over 90%), high yields and faster reaction times; and whereas Bacskai must heat his reaction medium to promote the reaction, the reaction of the invention is so fast as actually to require some cooling. A still further advantage of the invention is that it is performed by admixing two clear solutions, each of which may be formed instantaneously. This lends itself to continuous operation far better than the Bacskai operation or those other processes described in the art where the alkyl aluminum compound and titanium compound are premixed, sometimes with prolonged aging periods and heating.

Reference is also made to page 36, Table 1, of the Beynon et al. reference cited above. The lengthy reaction times reported in the table, e.g. 22 hours, are far slower than that achieved by the practice of this invention. It is therefore apparent that the mode of catalyst addition, as well as the presence of the organic halide component, are key to the advantages obtained by the subject process.

DETAILED DESCRIPTION OF THE INVENTION

The initial step in performing the instant invention is the blending of the organic halide and the transition metal compound; most preferably, this is done in the monomer. The temperature of the blending and the relative amount of each component are not critical, the latter amounts being determined by the overall ratio of each of the three components selected for the particular polymerization.

In the process of the invention the overall active halogen to aluminum ratio should be from 2.5:1 up to 25:1, preferably about 3:1 to 10:1. The active chlorine may be introduced into the system not only from the organic halide and the transition metal chloride but also with the alkyl aluminum compound, as for example where the alkyl aluminum compound is diethyl aluminum chloride. The aluminum to transition metal molar ratio is advantageously between 10:1 and 1:10.

The active halogen to aluminum ratio is determined by first ascertaining the number of active halogens. In the case of the aluminum alkyl and the organic halide components, all of the halide atoms are active and therefore the active halogens in each is determined by multiplying the number of atoms of the halide in the component by the number of moles of the component present. In the case of the transition metal halide, since the $TiCl_4$ is reduced only to $TiCl_3$, there is only one active halide for each active mole of the transition metal halide. After the total active halogens are determined, this total is divided by the number of equivalents of aluminum present. The latter is determined by multiplying the number of atoms of aluminum in the aluminum alkyl component by the number of moles of such component which are present in the catalyst. The following table shows examples of this calculation:

| Number of Moles of Catalyst Component | Halogen/Aluminum Ratio |
|---|---|
| $(C_2H_5)_3Al + TiCl_4 + 3RCl$ | 4/1 |
| $(C_2H_5)_2AlCl + 2TiCl_4 + RCl$ | 4/1 |
| $(C_2H_5)_3Al_2Cl_3 + TiCl_4 + 3RCl$ | 3.5/1 |

While temperature is not critical, the broad range being 0° to 200° C., it is preferably from 0° to 100° C., with 30° to 50° C. being most convenient.

As noted above, the alkyl aluminum compound is preferably initially blended with the monomer. In practice, the level of the alkyl aluminum compound to olefin in the final reaction mixture should be at least 0.1 wt. % based on total monomer. Preferably, from 0.1 to 5 wt. % is employed. Since, as in the case of the blending of the organic halide and the transition metal compound, no reaction takes place at this point, this step is easily performed.

The alkyl aluminum component may be represented by the formula $R_3Al_2X_3$ or $R_nAlX_{(3-n)}$, where X is a halogen, preferably chlorine, and R is an alkyl group containing from 1 to 12 carbon atoms. Examples of such compounds include alkyl aluminum sesquichloride, dialkyl aluminum monochlorides, alkyl aluminum dichlorides, and trialkyl aluminum compounds. Specific examples include triethyl aluminum, diethyl aluminum chloride, dimethyl aluminum bromide, diisobutyl aluminum chloride, diethyl aluminum chloride, and ethyl aluminum sesquichloride.

While it is preferable to admix the components in the monomer, the critical feature of the invention is to avoid the interaction of the three components prior to the contact with the feed and to avoid the use of an extraneous solvent. It has been found that premixing of the catalyst components in the ratios used in the instant invention, in the absence of monomer, is extremely detrimental. While the reason for this is not fully understood, it is believed that the catalyst formed has an extremely limited lifetime and that by the time the monomer is contacted with the catalyst, its activity has deteriorated substantially.

The organo-halides of the instant invention may be primary, secondary or tertiary aliphatic compounds, allylic halides or benzylic halides. No more than one halide should be present on each carbon atom. Aromatic halides are not operable. Generally, based on total monomer, from about 0.1 to 10 wt. % of the organohalide are used. Typical compounds include t-butyl chloride; t-butyl iodide; allyl chloride; methallyl chloride; methallyl iodide; benzyl chloride; benzyl iodide; 1-chloro-2-phenylethane; 1,2-dibromo-1-phenylethane; and 1,2,5,6-tetrachloro-cyclooctane. Also usable are higher molecular weight saturated or unsaturated molecules which have been halogenated to contain an average of one or more halogen atoms per molecule, for instance, chlorinated mineral oil, brominated high molecular weight poly alpha-olefins, chlorinated wax, rubbers or plastics, so long as the resultant products have solubility in alpha-olefins.

The transition metal component may be represented by the general formula: $MX_a$ where M equals a transition metal of Groups IV-B, V-B, VI-B and VIII of the Periodic System such as Ti, Zr, V, Cr, Mo, W and Fe, preferably Ti; X equals a halide, preferably Cl; and small a equals valence of M, e.g. 2 to 4. The preferred compound is titanium tetrachloride. Examples of other metal halides which may be employed include $ZrCl_4$, $VCL_4$ and $CrCl_3$. Based on the total monomer employed, from about 0.1 to 5 wt. % of the transition metal should be present.

To initiate the reaction of the invention, the mixture of the two catalyst components, preferably dissolved in the monomer, is combined with the monomer containing the alkyl aluminum component in a stirred autoclave or a pipe reactor. The reaction is very rapid and continuous polymerization can be achieved by removing the reaction mixture at the same rate the feed ingredients are being introduced. As will be readily understood by those skilled in the art, longer residence times may be used to produce higher viscosity oligomers. This can be accomplished by using larger reactor size or by reducing the feed rate. Conversely, with a given catalyst combination, the low residence times and higher temperatures can be utilized to produce lower viscosity fluids.

The monomers of use in this invention are those normally polymerizable by cationic (acid) catalysis. While, as noted above, alpha-olefins of $C_3$ to $C_{14}$ carbon atoms per molecule can be used, homopolymers having from $C_6$ to $C_{12}$ are preferred because they are easily handled liquids forming oligomers with excellent properties. Copolymers from blends of low molecular weight and high molecular weight monomers are useful and in certain instances form copolymers having properties superior to mixtures of their homopolymers.

Aside from straight-chain alpha-olefins, terminal olefins with branching can be polymerized using the methods of the instant invention. For instance, useful oligomers can be made from vinylidene-type monomers, such as 2-methylpropene (isobutylene), 2-ethylhexene-1, 2-butyloctene-1 and the like. Monomers having terminal double bonds and branches remote from the unsaturation may also be easily polymerized. An example of such a monomer would be 4-methylhexene-1.

Monomer consumption is normally greater than 95% and usually greater than 99%. The reaction may be stopped with water or a low molecular weight alcohol, followed by a catalyst removal step, such as an aqueous wash. Other methods of catalyst removal, such as filtration, absorption or centrifugation, can also be utilized. The product is usually subjected to an evaporative distillation to remove unreacted monomer or low boiling oligomers (e.g., below $C_{20}$) thereby insuring low volatility in the final product. The oil is optionally hydrogenated before or after distillation by conventional methods employing a hydrogenation catalyst and hydrogen for production of fluids having improved oxidation stability. Normally, an iodine number below 5 and preferably below 2 will produce an oligomer with excellent oxidation stability as illustrated in U.S. Pat. No. 4,110,234.

As is obvious to one skilled in the art, a variety of useful functional fluids can be prepared utilizing various mixtures of the above monomers.

As with all polymerizations involving organometallic catalysts, all ingredients and equipment used should be as free from air, moisture and other potential catalyst poisons as possible. Equipment can be dried by heat and vacuum while monomers can be distilled, passed through desiccant columns or stored over desiccants. Manipulation of the ingredients before and during polymerization should stress anaerobic conditions and inert gas atmospheres where necessary.

The temperatures operative in the practice of this invention normally range from 0° C. to 200° C., although temperatures outside this range can be utilized. In nonadiabatic polymerizations, heat transfer capability may be necessary to maintain steady state conditions.

The invention is further illustrated by the following examples which should not be construed to limit the scope of the invention.

EXAMPLE I

This example illustrates the preparation of an oligomer of decene-1 utilizing a catalyst system based on an alkyl aluminum compound, a titanium halide and an alkyl halide.

A dry nitrogen filled 4-necked 500 ml round bottomed flask was fitted with:

(1) A 125 ml dropping funnel having a pressure equalizing side arm and stopper.

(2) A similar dropping funnel connected to a nitrogen source and bubbler to insure a slight nitrogen pressure in the flask.

(3) A thermometer.

(4) An overhead mechanical stirrer.

Beneath the flask was placed a bath of cold water on a jack permitting periodic cooling of the flask as required.

Into dropping funnel (1) was syringed 95 ml of previously dried decene-1 and 10 ml of a 1.6 molar solution of triethyl aluminium (TEA) in hexane. Into dropping funnel (2) was syringed 105 ml of decene-1 and 3.92 ml (0.048 mole) of allyl chloride and 1.76 ml (0.016 mole) of $TiCl_4$. The contents of funnels (1) and (2) were added dropwise to the stirred flask at such a rate that addition was completed in 90 minutes. During the addition period, the temperature was maintained at 42±2° C. by raising or lowering the water bath. After the addition was completed, the reaction mixture was stirred for an additional 15 minutes after which 5 ml of methyl alcohol were added to destroy the catalyst. Precipitated residues were then removed by passing the slurry through a bed of F-20 alumina (Aluminum Company of America). The clear crude liquid oligomeric product was then subjected to a vacuum distillation to remove any constituents boiling below 150° C. at 0.1 millimeter. The residual product, obtained in over 90% yield, had a kinematic viscosity at 100° C. (K.V._{100}) of 12.51 cSt., a K.V._{40} of 81.90 cSt., and a viscosity index of 151.

In an otherwise identical experiment, 7.84 ml of allyl chloride (0.096 mole) was used. The resultant fluid was considerably more viscous, having a K.V._{100} of 39.70, a K.V._{40} of 409.53, and viscosity index of 146.

In summary:

| TEA, mmol | TiCl$_4$, mmol | Allyl Chloride, mmol | K.V.$_{100}$ | K.V.$_{40}$ | VI |
|---|---|---|---|---|---|
| 16 | 16 | 48 | 12.51 | 81.90 | 151 |
| 16 | 16 | 96 | 39.70 | 409.53 | 146 |
| 16 | 0 | 48 | no reaction | | |
| 16 | 0 | 96 | no reaction | | |

Thus, the addition of TiCl$_4$ in the above experiments produces a rapid oligomerization of decene to produce low viscosity oligomers whose viscosity is somewhat controllable by allyl chloride level. When the experiments were repeated in the absence of TiCl$_4$, no reaction occurs. If TEA and TiCl$_4$ are used as catalyst in the absence of allyl chloride, a very slow (ca. 24 hour) conversion of decene to polymer occurs. In the article by Beynon et al. cited above, at the temperature and at the TEA/TiCl$_4$ ratios used in this example, the slow formation of "waxy solids" in low yields was reported. Repeating the experiment herein, a very low yield of sticky rubber was obtained after 24 hours.

EXAMPLE II

This example illustrates the oligomerization of decene-1 utilizing a catalyst system composed of diethyl aluminum chloride (DEAC), TiCl$_4$ and tertiary butyl chloride (TBC). Following exactly the procedures outlined in Example I, the following combinations were examined, and the resultant fluids had the viscosities listed below:

| | DEAC, mmol | TiCl$_4$, mmol | t-C$_4$H$_9$Cl, mmol | K.V.$_{100}$ | K.V.$_{40}$ | V.I. |
|---|---|---|---|---|---|---|
| A. | 24 | 0 | 24 | no reaction | | |
| B. | 24 | 0 | 72 | 26.08 | 235.95 | 143 |
| C. | 24 | 24 | 72 | 37.69 | 377.86 | 147 |
| D. | 24 | 24 | 24 | 15.31 | 115.09 | 139 |

As with TEA and TiCl$_4$ in Example I, the DEAC and TiCl$_4$ used produce only a slow Ziegler polymerization in the absence of tertiary butyl chloride. Note that Run A (above) produced no oligomer but that the addition of TiCl$_4$ in Run D promoted a rapid polymerization.

In contrast to the allyl chloride of Example I, tertiary butyl chloride acts as a co-initiator with TEA (as in Run B) and the addition of TiCl$_4$ (as in Run C) increases the viscosity of the product.

EXAMPLE III

The example illustrates the viscosity lowering achieved by the addition of TiCl$_4$ to a bromine based catalyst combination.

Following the procedures of Example I, the following combinations were examined and the resultant fluids had the viscosities listed below:

| | Et$_3$Al$_2$Br$_3$, mmol | Br$_2$, mmol | TiCl$_4$, mmol | K.V.$_{100}$ | K.V.$_{40}$ | V.I. |
|---|---|---|---|---|---|---|
| A. | 8 | 58.5 | 24 | 47.10 | 483.50 | 154 |
| B. | 8 | 39 | 0 | 81.35 | 947.49 | 166 |
| C. | 8 | 78 | 0 | 82.86 | 939.72 | 170 |

In the experiment, liquid bromine was added slowly to decene in funnel (2) to prepare 1,2-dibromodecane (in situ) which was the true cocatalyst with ethyl aluminum sesquibromide. Runs B and C above show the insensitivity of the catalyst combination to the level of bromine added. This demonstrates the viscosity lowering effected by TiCl$_4$. This permits changing the viscosity in a polymerization product by altering the TiCl$_4$ level, thereby eliminating the need to change such variables as the rate of addition, temperature or alkyl aluminum level.

The effect observed here is in contrast, unexpectedly, to the viscosity increasing effect seen in Example II (Run B vs. Run C).

What is claimed is:

1. A process for oligomerizing an alpha-olefin which comprises contacting a transition metal halide and an organic halide with an alpha-olefin and thereafter an alkyl aluminum compound in a reaction zone, the mole ratio of the active halogen to aluminum being from 2.5 to 25, and oligomerizing said alpha-olefin to form oligomers having a molecular weight of from about 500 to 5000.

2. The process of claim 1 wherein the transition metal halide and the organic halide are admixed with alpha-olefin and such admixture is added to the reaction zone.

3. The process of claim 1 wherein the concentration based on alpha-olefin is from 0.1 to 10 wt. % of organic halide, 0.1 to 5 wt. % of the transition metal halide, and 0.1 to 5 wt. % of the alkyl aluminum compound, and the molar ratio of the aluminum to the transition metal is from 10:1 to 1:10.

4. The process of claim 1 wherein the alpha-olefin contains from 3 to 14 carbon atoms.

5. The process of claim 1 wherein the oligomerization takes place at a temperature from 0° to 200° C.

6. The process of claim 1 wherein the transition metal halide is titanium tetrachloride; the organic halogen compound is allyl chloride or t-butyl chloride; and the alkyl aluminum is triethyl aluminum or diethyl aluminum chloride, ethyl aluminum sesquibromide or ethyl aluminum sesquichloride.

* * * * *